United States Patent
Pursifull et al.

(10) Patent No.: US 9,329,160 B2
(45) Date of Patent: May 3, 2016

(54) HUMIDITY SENSOR DIAGNOSTIC METHOD USING CONDENSATION CLEARING HEATER

(71) Applicant: Ford Global Technologies, LLC, Dearborn, MI (US)

(72) Inventors: Ross Dykstra Pursifull, Dearborn, MI (US); Imad Hassan Makki, Dearborn Heights, MI (US); Timothy Joseph Clark, Livonia, MI (US); Michael James Uhrich, West Bloomfield, MI (US); Pankaj Kumar, Houston, TX (US); Yong-Wha Kim, Ann Arbor, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 434 days.

(21) Appl. No.: 13/857,884

(22) Filed: Apr. 5, 2013

(65) Prior Publication Data
US 2014/0298880 A1  Oct. 9, 2014

(51) Int. Cl.
*G01N 33/00* (2006.01)

(52) U.S. Cl.
CPC .......... *G01N 33/0006* (2013.01); *G01N 33/007* (2013.01); *G01N 33/0008* (2013.01)

(58) Field of Classification Search
CPC .......... G01N 33/0006; G01N 27/4175; G01N 21/3504; G01N 33/007; F02D 41/1495
USPC .............. 73/1.06, 1.02, 432.1, 865.9, 335.01; 374/141, 142, 144; 361/286; 701/29.1–31.2
See application file for complete search history.

(56) References Cited

U.S. PATENT DOCUMENTS

| | | | |
|---|---|---|---|
| 6,073,480 A | 6/2000 | Gokhfeld | |
| 7,077,004 B2 * | 7/2006 | Mitter | G01N 27/223 73/29.01 |
| 7,176,700 B2 | 2/2007 | Itakura et al. | |
| 7,418,957 B2 * | 9/2008 | Abe | F02D 41/1494 123/697 |
| 7,644,608 B2 * | 1/2010 | Mc Lain | F02D 41/222 73/114.31 |
| 7,918,129 B2 * | 4/2011 | Coppola | F01P 11/16 73/114.68 |
| 8,315,759 B2 * | 11/2012 | Bauerle | F02D 41/222 123/677 |
| 8,959,910 B2 * | 2/2015 | Rollinger | F02D 41/22 60/602 |
| 2009/0254245 A1 | 10/2009 | Bauerle | |

OTHER PUBLICATIONS

Pursifull, Ross Dykstra et al., "Humidity Sensor Diagnostics," U.S. Appl. No. 13/774,319, filed Feb. 22, 2013, 46 pages.
Pursifull, Ross Dykstra et al., "Humidity Sensor Diagnostics," U.S. Appl. No. 13/774,282, filed Feb. 22, 2013, 48 pages.
Pursifull, Ross Dykstra et al., "Humidity Sensor and Engine System," U.S. Appl. No. 13/865,853, filed Apr. 18, 2013, 34 pages.

* cited by examiner

*Primary Examiner* — Peter Macchiarolo
*Assistant Examiner* — Yusuf O Siwoku
(74) *Attorney, Agent, or Firm* — Julia Voutyras; Alleman Hall McCoy Russell & Tuttle LLP

(57) ABSTRACT

A diagnostic method for a capacitive humidity sensor comprising a heater, and a capacitance-sensing element that individually identifies heater, temperature-sensing element, or capacitance-sensing element degradation. By this method, individual elements of the sensor may be replaced or compensated for to allow for further operation.

20 Claims, 12 Drawing Sheets

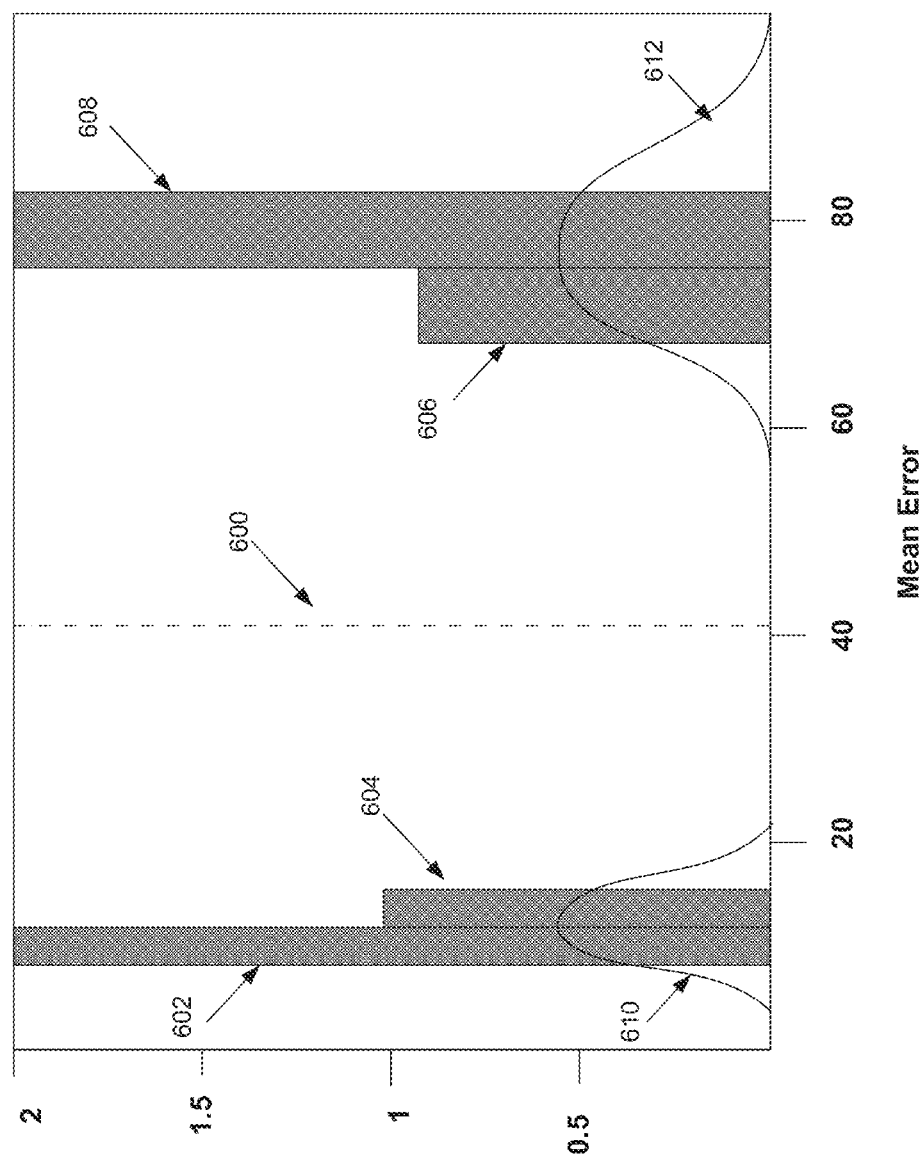

HUMIDITY SENSOR DIAGNOSTIC METHOD USING CONDENSATION CLEARING HEATER

BACKGROUND AND SUMMARY

Engine systems may employ humidity sensors to monitor the operating conditions of the engine. Humidity sensors located within the intake manifold can factor into a determination of an air-to-fuel ratio, meter an amount of exhaust gas recirculation in an intake, and others.

Humidity sensors may measure relative humidity, absolute humidity, or specific humidity.

One example humidity sensor degradation diagnostic method is disclosed in U.S. Pat. No. 6,073,480 wherein fault within a capacitance humidity sensor is determined by using a condensation heater coupled to the humidity sensor to increase the local temperature and thus the corresponding humidity. Degradation is then determined by comparing the capacitance of the sensor before and after the heater is activated. Specifically, U.S. Pat. No. 6,073,480 determines capacitance humidity sensor degradation by cycling between temperatures above and below a dew point and compares the change in relative humidity to the change in capacitance. If the capacitance does not change an expected amount between an above-dew-point and a below-dew-point temperature, sensor degradation is indicated.

However, the inventors herein have recognized some potential issues with the above approach. Namely, the degradation indication relies on a properly functioning heater and temperature sensor. Heater or temperature sensor degradation may therefore be misdiagnosed as sensor capacitor degradation, or vice versa. The above method also relies on a modeled local temperature in response to the activation of a heater; however the temperature near the humidity sensor is not isolated and may be affected by atmospheric temperature or the heat of the engine, leading to inaccurate results.

The inventors recognized that the above issues may be addressed specifically in systems with a condensation-heater and temperature sensor coupled to the humidity sensor. Embodiments of these systems use the absolute humidity detected, a measured temperature, and an assumed or measured total pressure to determine other measures of humidity. By a similar method, absolute humidity can be found to be a function of temperature, total pressure, and specific humidity.

For example, specific humidity (also known as humidity ratio) is not affected by ambient temperature or pressure, because it is a mass ratio of water to dry air. Therefore, the relative humidity for a given absolute humidity can be modeled as a function of pressure and temperature. The inventors found that by comparing the modeled output of the humidity sensor to the actual output of the humidity sensor, degradation can be determined if the difference between the modeled output and actual output surpasses a margin of error threshold. In other embodiments using particular humidity sensors, the relative humidity may be calculated as a function of the specific humidity and the measured temperature. Humidity sensor degradation may then be indicated if the calculated relative humidity exceeds the known limits for relative humidity.

In one embodiment, a method, comprises operating a sensor in an engine intake, a housing of the sensor including a temperature-sensing element, a heater, and a capacitance-sensing element; and individually distinguishing between each of heater, temperature-sensing element, and capacitance-sensing element degradation. In this way, it is possible to provide accurate diagnostics and prognostics.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF FIGURES

FIG. 6 graphically depicts the average error of four example humidity sensor outputs.

DETAILED DESCRIPTION

Figure 1:
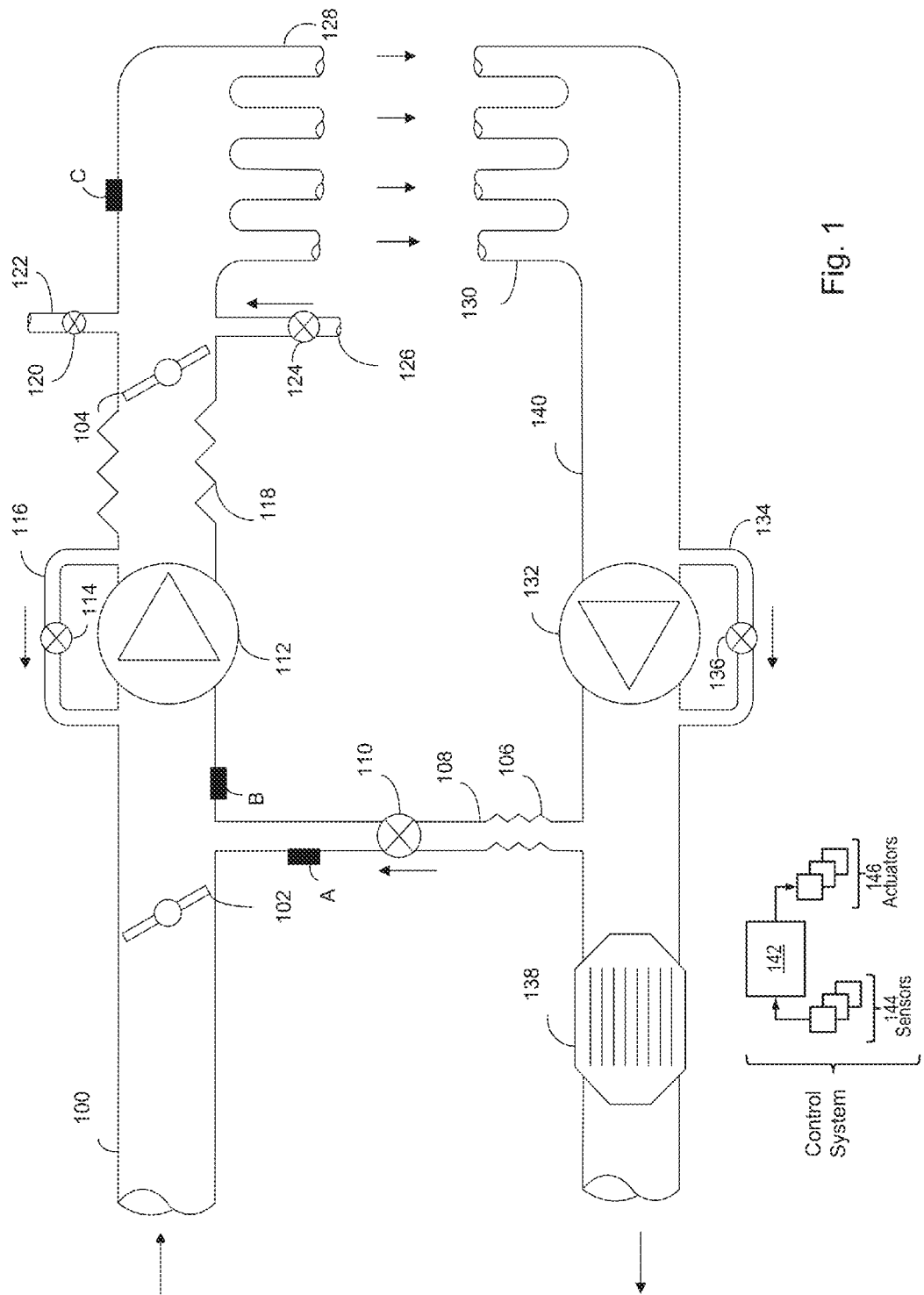
FIG. 1 shows a schematic embodiment of an intake and exhaust system.

EGR systems may be incorporated into engine systems to lower emissions and increase fuel efficiency. The amount of EGR delivered to an engine may depend on several operating conditions including the properties of the exhaust gas recirculated into the intake. Exhaust may be recirculated to control emissions. The amount of EGR recirculated may also be adjusted to achieve an engine torque. These adjustments may be made in response to sensors in an EGR path or in the intake and may include humidity sensors that may be employed to determine the air charge.

The concentration of various emissions such as particulate matter and $NO_X$ may be determined at point throughout the intake and exhaust system and may vary in response to operating conditions. $NO_X$ concentration may increase with combustion temperature within the engine system and decrease with diluents such as humidity. Therefore, engine operating conditions may be adjusted in response to humidity to achieve an emission rates.

Humidity may be monitored using one of three different measurements.

Relative humidity is defined as the ratio of partial pressure of water vapor to the saturated vapor pressure at a specified temperature. Relative humidity may be computed from a dew point sensor's measurement of dew point. This type of sensor maintains a mirror at a dew point temperature and senses the amount of condensation that forms on the chilled mirror. Relative humidity may also be computed from wet bulb and dry bulb measurements. Relative humidity may be computed from the evaporative cooling effect observed on a wet surface.

Absolute humidity is a measure of the amount of water per unit volume of a total mixture of air and water vapor. Water vapor content sensors may be used to measure absolute humidity. These sensors include capacitance humidity sensors wherein the amount of water between the electrodes of the capacitor affects the dielectric constant of the capacitor and thus the capacitance. Further, water vapor sensors may measure a temperature and measure or assume a total pressure to compute other measures of humidity such as relative or specific humidity.

Specific humidity may be defined as the ratio of an amount of water to an amount of dry air in a given volume. As explained herein, using the principles of thermodynamics, the specific humidity may be found to be a function of the relative humidity and other parameters. Specific humidity is particularly useful in determining levels of air dilution with water.

Turning now to additional details regarding the different measures of humidity, the absolute humidity of a sample may be defined by:

$$H_{ABS} = \frac{m_{H_2O}}{V_{air}}.$$

Relative humidity of a given sample is the ratio of the partial pressure of water vapor within the mixture to a known value of the saturated vapor pressure of the liquid in thermodynamic equilibrium at the given temperature:

$$H_R = \frac{\text{partial pressure of water vapor}(P_{H_2O})}{\text{saturated vapor pressure at that temperature}(P_{Sat})}.$$

Specific humidity of a sample is the ratio of the mass of water vapor within the sample to the mass of dry air within the sample:

$$H_S = \frac{m_{H_2O}}{m_{air}}.$$

The mass of $H_2O$ may be a function of its molar mass (18 g/mol), temperature, and partial pressure. Similarly the mass of air may be found to be a function of molar mass (29 g/mol), temperature, and partial pressure. The partial pressure of air within a sample containing water vapor may be found to be equal to the partial pressure of the ambient air minus the partial pressure of water. Thus, the specific humidity may be represented by the equation below:

$$H_S = \frac{P_{H_2O} \times 18 \text{ g/mol}}{(P_{ambient} - P_{H_2O}) \times 29 \text{ g/mol}} \times 1000 \text{ g/kg}.$$

Relative humidity may also be found to be a function of the specific humidity:

$$H_R = \frac{P_{H_2O}}{P_{Sat}} = \frac{P_{ambient}}{P_{Sat}} \left( \frac{1}{1 + \frac{620.68}{H_S}} \right).$$

This relationship may be represented logarithmically:

$$\log(H_R) = \log(P_{ambient}) - \log(P_{Sat}) + c_1 \log(H_S) + c_2.$$

The pressure of a saturated system at a given temperature is in the denominator of this ratio, thus the relative humidity cannot surpass 100%, as partial pressure is directly related to percent saturation. Therefore, relative humidity has an upper limit of 100%. The lowest relative humidity observed at the earth surface is approximately 20%.

Specific humidity may be a function of absolute humidity and temperature and may be expressed in most atmospheric conditions as:

$$H_S = \frac{H_A RT(P_{ambient} - P_{H_2O})}{M}.$$

Relative humidity may similarly be expressed as:

$$H_R = \frac{P_{ambient}}{P_{Sat}} \frac{1}{1 + \frac{620.68 \text{ M}}{H_A RT(P_{ambient} - P_{H_2O})}}$$

Here R is the Rydberg constant and T is the temperature. Thus there is no net effect on either $H_S$ or $H_T$ due to temperature.

If heat is added to a sample of air the density of sample will decrease, thus the mass of water vapor within a given volume of air will decrease. This causes a decrease in the absolute humidity measurement due to its volume dependence. However, the ratio between the mass of water vapor and the mass of dry air will remain constant as the temperature change will equally affect both masses. Therefore, the specific humidity and relative humidity remain unaffected by the change in temperature.

Capacitance humidity sensors measure absolute humidity by placing the capacitor's electrode within a sample to be measured, filling the air gap separating the electrodes. Water in liquid or vapor form has dielectric capabilities so that, when placed between two plates of a capacitor, its dipole moment will align along the electric field between electrodes lowering the electric field strength between the electrodes. The presence of the dielectric heightens the capacitance. Capacitance may then be measured by monitoring the current through a circuit with known voltage potentials (normally done with an AC circuit)

The amount of dielectric between the electrodes is directly proportional to the increase in capacitance. Therefore, if absolute humidity increases, the mass of water present within the volume between the capacitors electrodes increases consequently increasing capacitance. Similarly, if absolute humidity decreases, the mass of water present within the volume between the capacitor's electrodes decreases consequently decreasing capacitance. Thus, an expected change in absolute humidity can be modeled as a function of a change in temperature.

Figure 2:
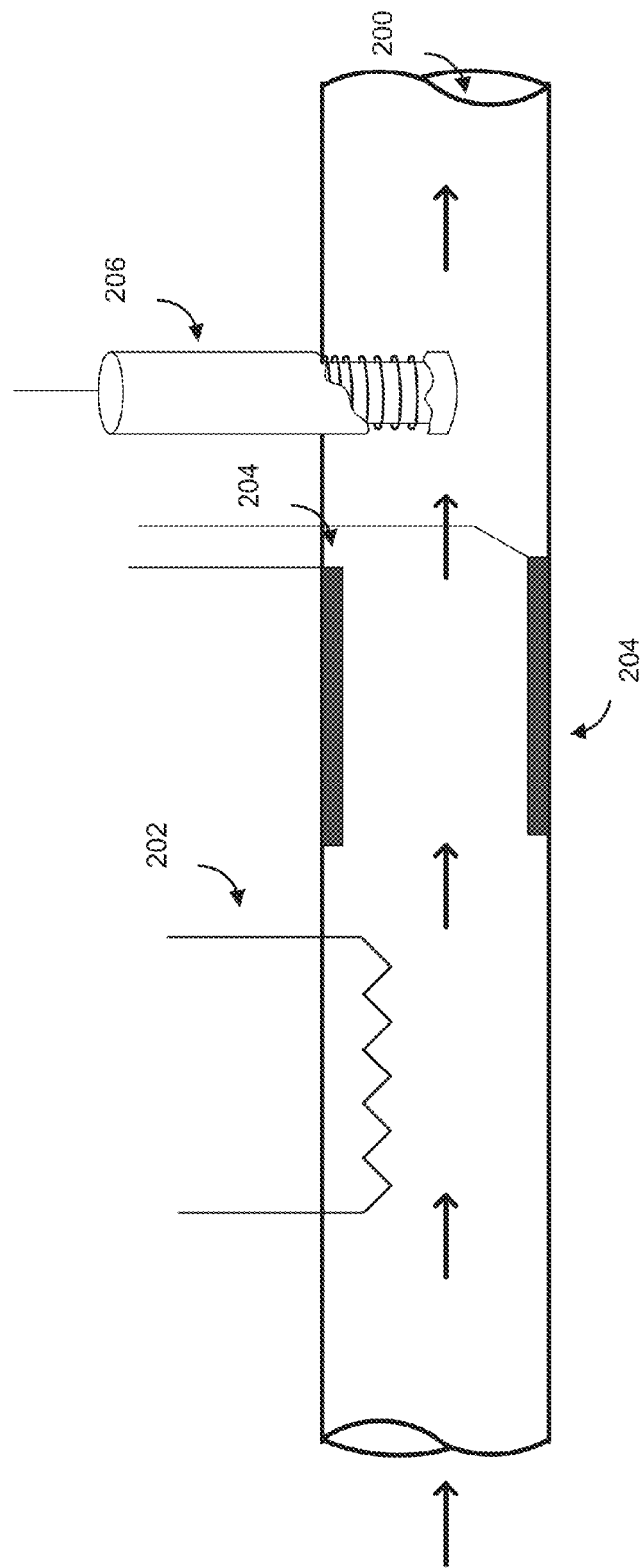
FIG. 2 shows a schematic embodiment of a humidity sensor.
Figure 3:
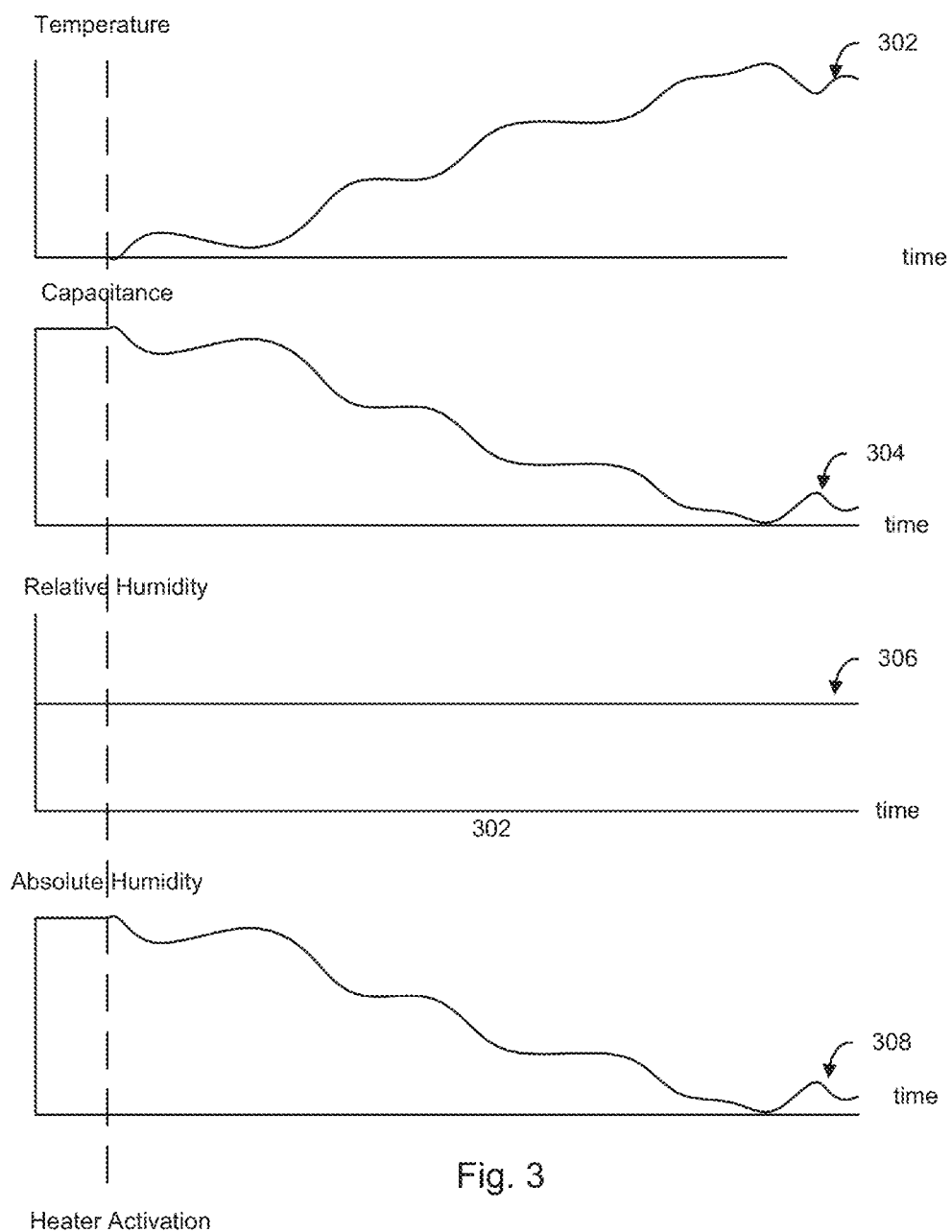
FIG. 3 graphically depicts example engine conditions as a function of time.
Figure 4A:
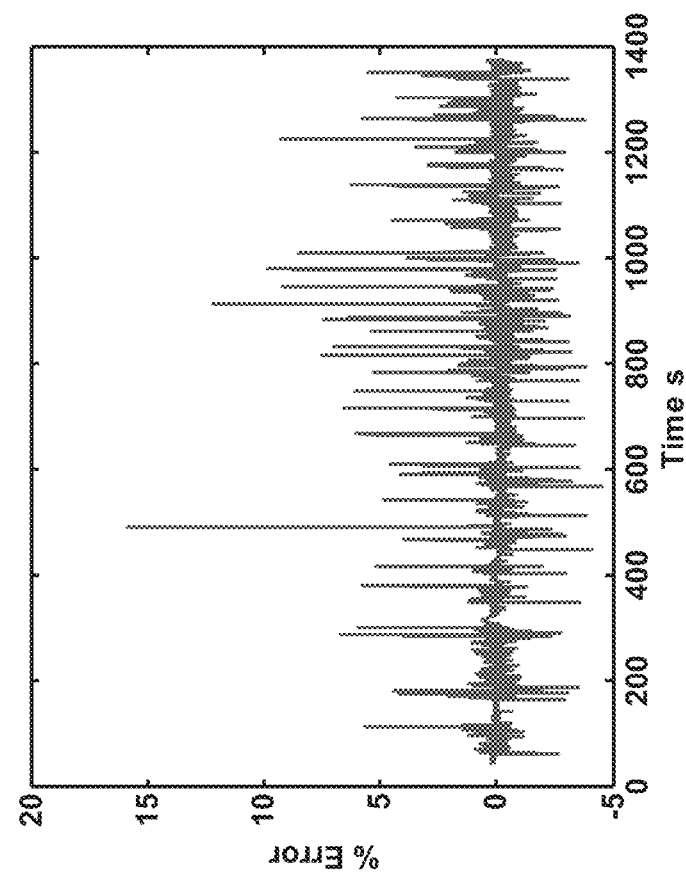
FIG. 4A graphically depicts an example relative humidity as a function of time for an actual humidity sensor output and a modeled humidity sensor output.
Figure 4B:
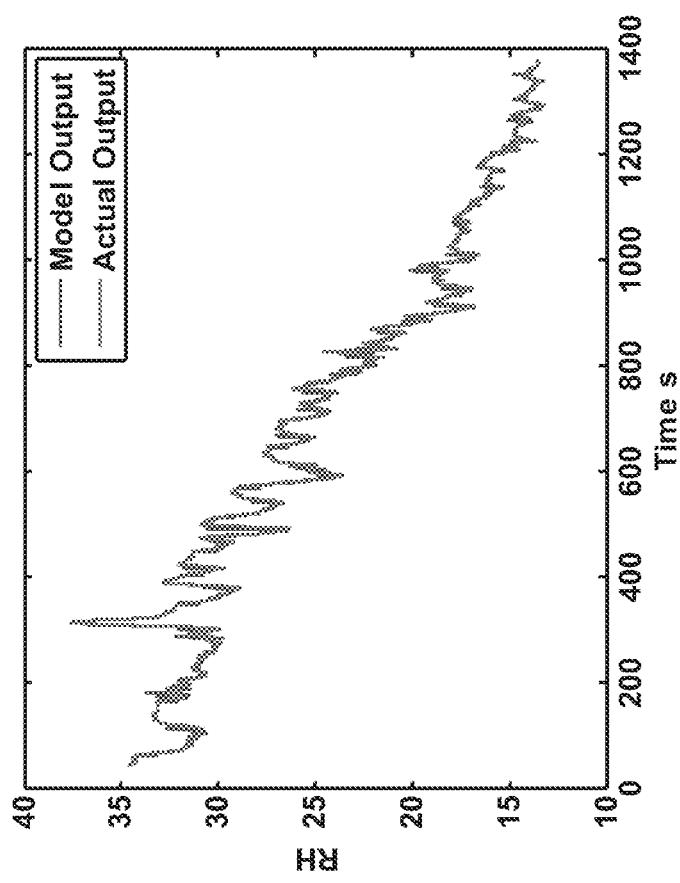
FIG. 4B graphically depicts the error between the actual humidity sensor output and the modeled humidity sensor output or FIG. 4A as a function of time.
Figure 5B:
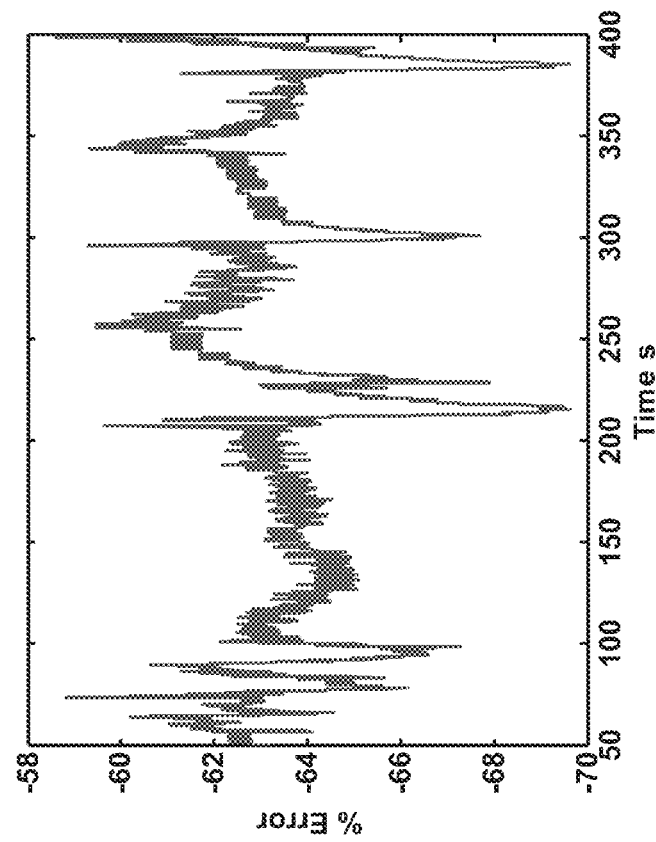
FIG. 5B graphically depicts the error between the actual humidity sensor output and the modeled humidity sensor output of FIG. 5A.
Figure 5A:
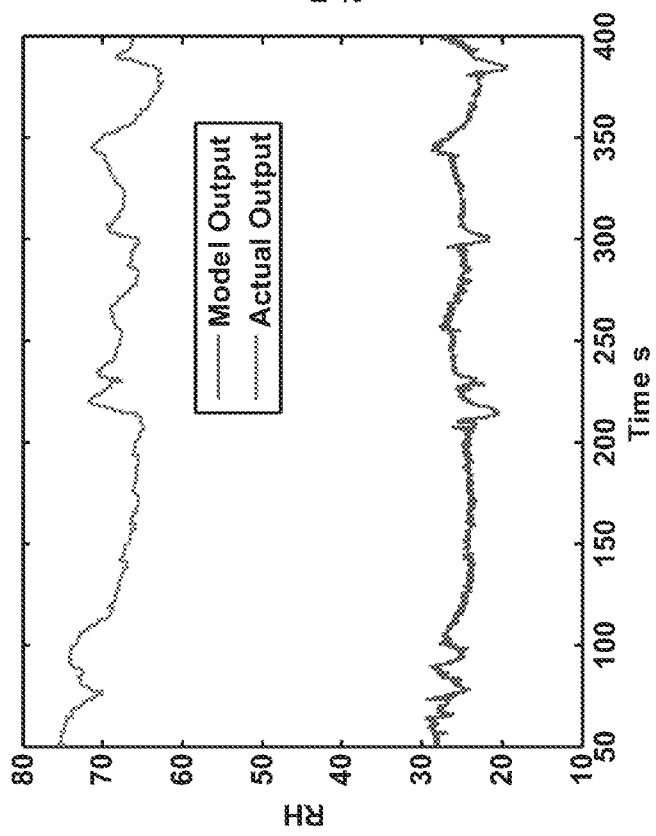
FIG. 5A graphically depicts an alternate example relative humidity as a function of time for an alternate actual humidity sensor output and an alternate modeled humidity sensor output.

FIG. 1 shows an example intake and exhaust system for a four cylinder inline engine that may be included in the propulsion system of a vehicle. FIG. 2 shows an example humidity sensor including a condensation heater a capacitance sensor, and a temperature sensor. The relationship between a capacitance, relative humidity, absolute humidity and temperature is shown for an example humidity sensor over a period of time is depicted in FIG. 3. FIG. 4A shows an example relative humidity for the output of an actual humidity sensor and a modeled humidity sensor over a period of time. The error between the two outputs in FIG. 4A is depicted in FIG. 4B. FIG. 5A shows an alternate example relative humidity for the output of an actual humidity sensor and a modeled humidity sensor over a period of time. The error between the two outputs in FIG. 5A is depicted in FIG. 5B. The average error for four example actual humidity sensor outputs and their corresponding modeled outputs (such as those depicted in FIG. 4A and FIG. 5A) is shown in FIG. 6.

Figure 7:
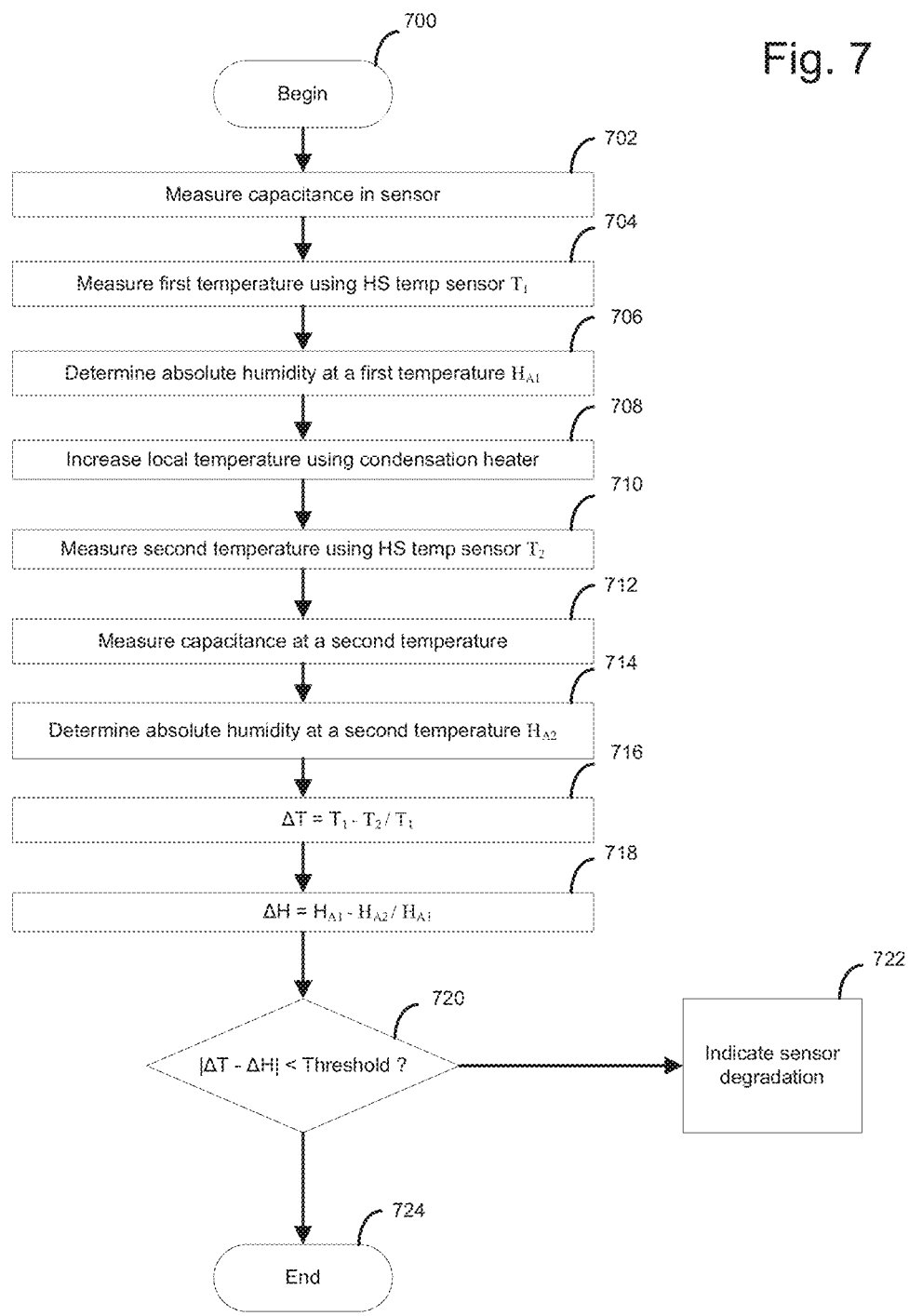
FIG. 7 is an example humidity sensor degradation diagnostic method.
Figure 8:
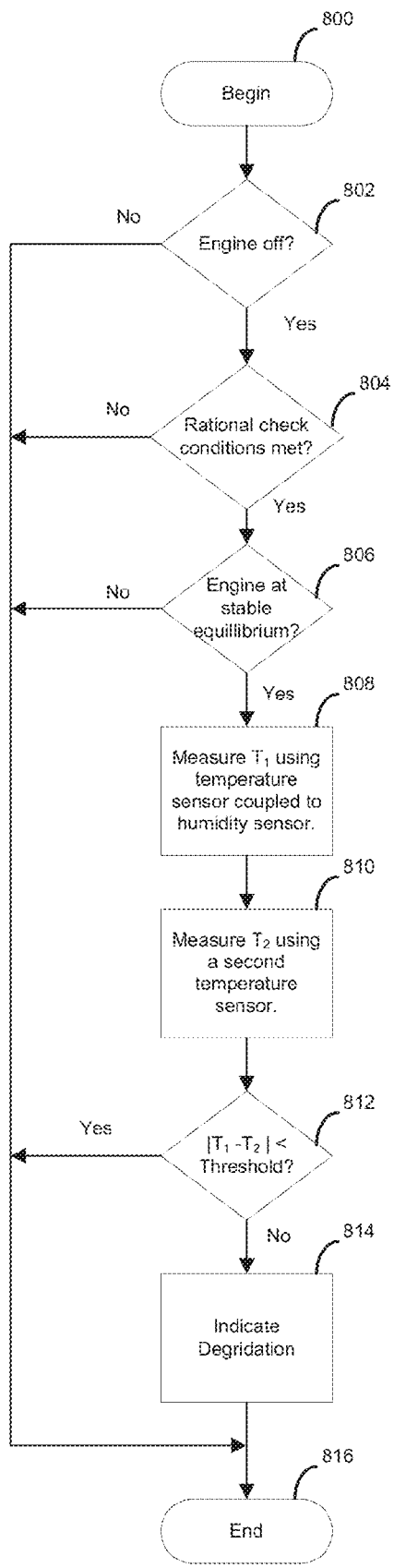
FIG. 8 is an example humidity sensor degradation diagnostic method.
Figure 9:
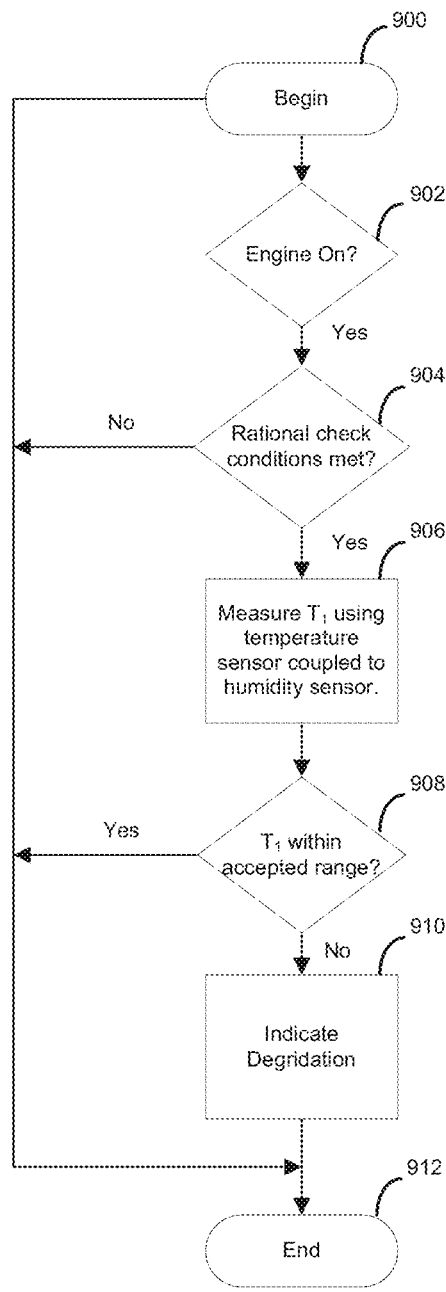
FIG. 9 is an example humidity sensor degradation diagnostic method.
Figure 10:
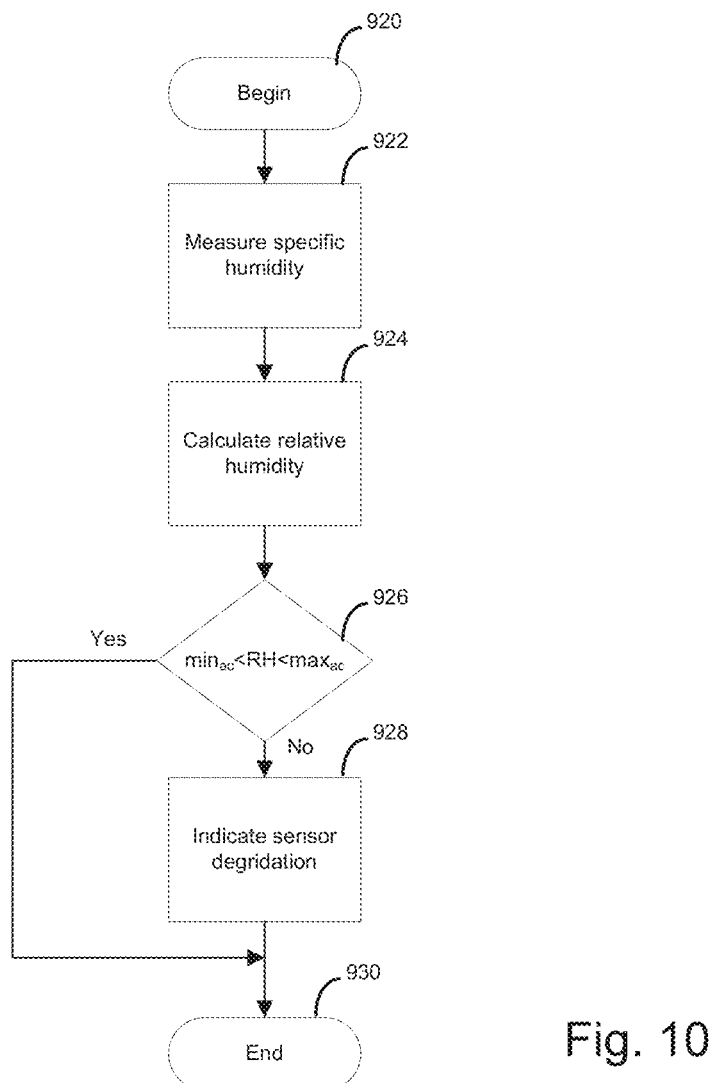
FIG. 10 is an example humidity sensor degradation diagnostic method.
Figure 11:
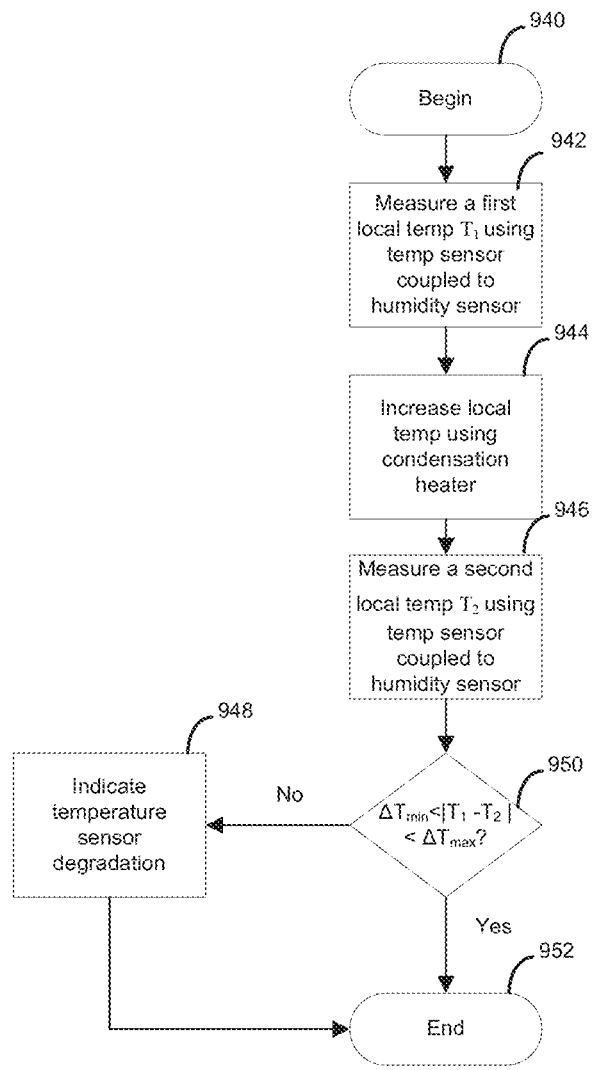
FIG. 11 is an example humidity sensor degradation diagnostic method.
Figure 12:
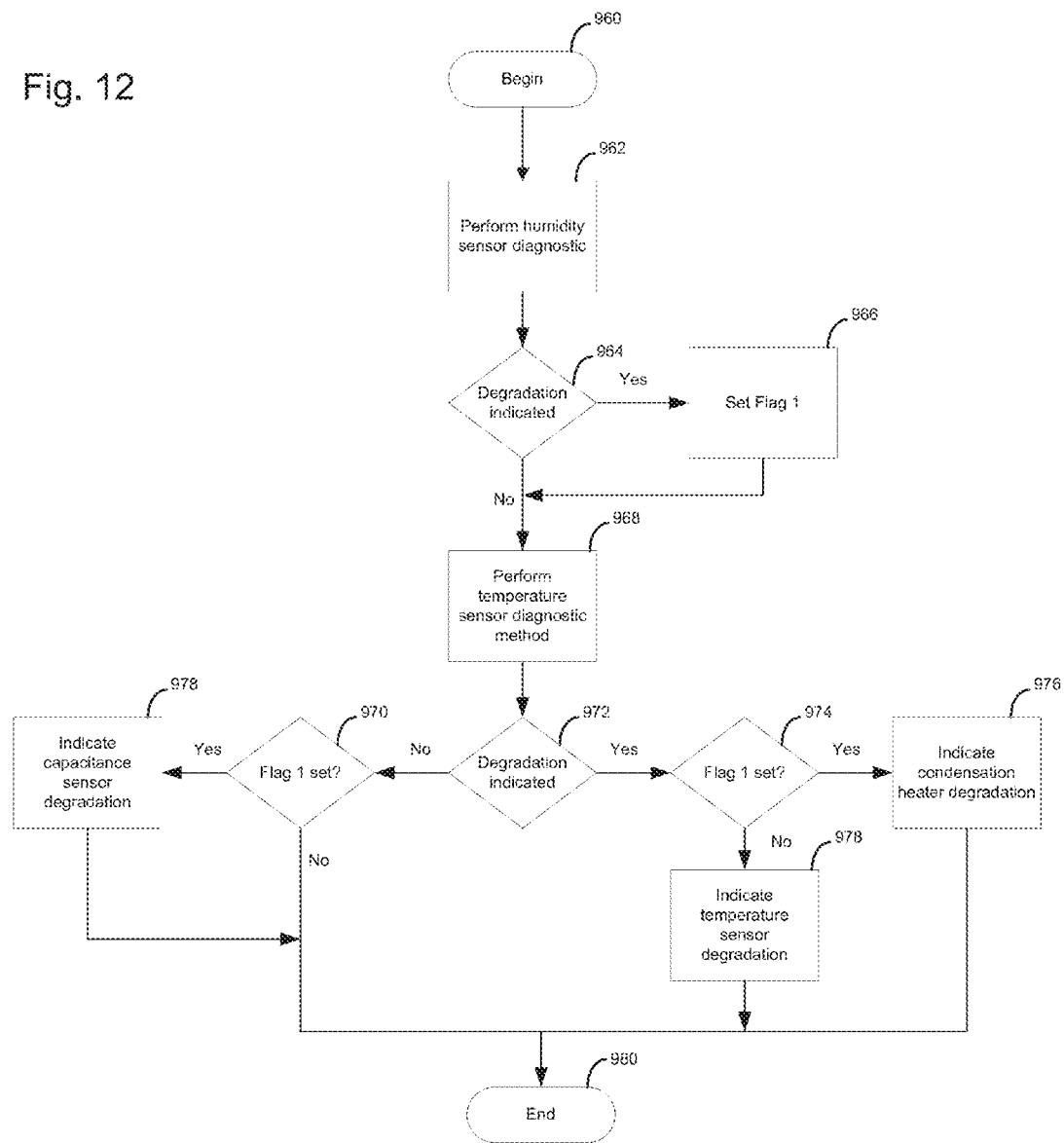
FIG. 12 is an example humidity sensor degradation diagnostic method.

Example embodiments of humidity sensor degradation diagnostic methods are shown in FIG. 7-12. In FIG. 7, an example method is shown that indicates humidity sensor degradation in response to temperature change. FIG. 8 shows an example method to diagnose degradation of the temperature sensor within a humidity sensor. FIG. 9 shows an alternate method to diagnose degradation of a temperature sensor within a humidity sensor. FIG. 10 shows a method to determine degradation of a humidity sensor in response to accepted relative humidity ranges. FIG. 11 shows an alternate method to diagnose temperature sensor degradation within a humidity sensor. FIG. 12 shows an example method to diagnose humidity sensor degradation as well as the component within the humidity sensor that is degraded.

The embodiment in FIG. 1 shows an example exhaust system of an engine that may be included in the propulsion system of a motor vehicle. The embodiment is compatible with a four cylinder inline engine. Air from the atmosphere may enter an intake pipe 100 and be throttled by low pressure throttle 102 actuated by control system 142 in response to engine load. Here air intake may be combined with recirculated exhaust gas in embodiments with EGR via EGR pipe 108. The flow of EGR gas into the aircharge may be metered by an EGR valve 110 actuated by control system 142. In turbocharged systems, aircharge may be compressed by compressor 112 receiving power from turbine 132. In some embodiments throttle 114 may control the recirculation of compressed aircharge into the compressor via compressor bypass 116 in response to operating conditions, actuated by control system 142. Air charge may then pass through charge air cooler 118. Compressed aircharge may subsequently be throttled by high pressure throttle 104. A crank case ventilation pipe 126 and/or one or more intake purges may be coupled to the intake system. Compressed aircharge may the enter intake manifold 128 coupled to the combustion chambers of the engine. Fuel may be injected into the air charge within the intake manifold 128 or within the combustion chamber.

Exhaust manifold 130 may be coupled to the combustion chambers. Downstream of the exhaust manifold 130, an exhaust pipe 140 may be coupled to turbine 132 providing power to compressor 112. Turbine bypass 134 may have an inlet coupled to exhaust pipe 140 upstream of the turbine and an outlet coupled to exhaust pipe 140 downstream of the turbine. The flow of high pressure exhaust gas through the turbine bypass 134 may be metered by a turbine bypass throttle 136 in response to operating conditions via the control system 142. Exhaust may be recirculated into the exhaust system via EGR pipe 108. One or more EGR coolers 106 may be coupled to the EGR pipe 108. In other embodiments the exhaust system may be coupled to the EGR pipe upstream or downstream of the turbine and the EGR pipe may be coupled to intake pipe 100 upstream or downstream of the compressor. Further, embodiments may include a multitude of combinations of the above EGR paths. Exhaust pipe 140 may be coupled to an emission control device 138 such as a catalytic converter or a particulate filter.

The system of FIG. 1 may have a multitude of sensors 144 communicatively coupled to control system 142. These sensors may include temperature sensors, pressure sensors, and humidity sensors. Humidity sensors may be located at several locations within the intake and exhaust system to determine humidity at various points and may communicate with the control system communicatively coupled to actuators that may be responsive to humidity. Three possible locations for humidity sensors are indicated by letters A, B, and C in FIG. 1. Embodiments may include sensors at A, B, C, other unspecified locations, or some combination thereof.

Humidity sensors that are located at positions at or near atmospheric pressure, such as an intake manifold upstream of a turbo charger, a relative humidity sensor may measure absolute humidity and augment that measurement with a predefined pressure value (generally ~103 kPa) to determine relative humidity. Thus, if the atmospheric pressure is known, a correction may be made for the difference between assumed pressure and actual pressure.

If a humidity sensor is placed in a location with dynamically changing pressures, the absolute humidity may be determined and the relative humidity may be augmented by a measured or calculated pressure. Pressure may be measured at or near the humidity sensor, it may also be calculated based on other measured conditions near the humidity sensor or a known relationship between actual humidity and other operating conditions or pressure measurements.

Let me say a word about relative humidity sensors commercially available to the automotive industry. They are typically truly absolute temperature sensors augmented with temperature sensors. They assume a pressure—typically 103 kPa. In the past, they have been always located in places were the pressure was atmospheric. Thus, if the atmospheric pressure was known, a corection could be made for the difference between assumed pressure and actual pressure. Since we are putting these humidity sensors in a location with dynamically changing pressures, it fundamentally changes how we have to compensate these sensors for actual pressure instead of anassumed single pressure.

A humidity sensor at location A may measure the humidity of exhaust gas to be recirculated into the intake. The humidity of EGR gas may be determinative of the water vapor content within the EGR gas as well as the concentration of various emissions being exhausted by the vehicle at the presiding operating conditions. Actuators 146 communicatively coupled to the control system may be responsive to a humidity sensor at location A. For example, if the humidity at A increases it may indicate increased water vapor concentration within the EGR gas. EGR throttle 110 may be actuated in response to the increase and may increase the amount of EGR gas recirculated into the intake. The control system may, for example, have instructions to actuate the EGR throttle to adjust emission rate, engine temperature, or engine torque.

A humidity sensor at location B may measure the humidity of the aircharge from the atmosphere that may contain an amount of EGR gas. A control system 142 may use the sensor at B to determine the water vapor content of air charge to be delivered to the engine or the atmospheric humidity. Further, actuation of low pressure throttle 102 or compressor bypass throttle 114 may be adjusted in response to atmospheric humidity to achieve an internal temperature, humidity, pressure, or combustion efficiency. Compressor bypass throttle 114 may increase an amount of air charge through compressor bypass 116 in response to increased humidity levels so as to prevent degradation to the compressor from condensation.

A humidity sensor at location C may determine the humidity of the compressed aircharge to be delivered to the engine and may determine the total fuel content from aircharge available for combustion. High pressure throttle 104 may be responsive to the humidity measured at location C and may adjust an amount of compressed air delivered to the intake manifold. Humidity at C may be influenced by the flows of crankcase vapor, brake booster air, or canister purge fuel/air mix that flow into the intake manifold.

FIG. 2 is a schematic depiction of an embodiment of a humidity sensor compatible with the disclosed method. Aircharge may flow through a passage 200, the sensor may be at an aforementioned sensor location. The humidity sensor disclosed may couple a heater 202, a capacitor 204, and a temperature sensor 206. The depicted temperature sensor 206 is a coiled resistance thermometer however other embodiments may use other temperature sensors such as alternate resistance thermometer configurations or a thermocouple. The heater depicted is a resistive heater; other embodiments may similarly use other heaters. The heater, temperature sensor, and capacitor may be aligned linearly such the air flowing past the heater may pass through the capacitor and thermally interact with the temperature sensor.

When activated, heater 202 may increase the local temperature within the humidity sensor. The increased local temperature may cause the aircharge within the humidity sensor, between the parallel plates of the capacitor 204 specifically, to expand. Because this expansion is homogenous, the amount of water vapor within the volume between the parallel plates may decrease causing a decrease in capacitance. Temperature sensor 206 may then measure the temperature of the air that has traversed the capacitor.

The relationship between components is depicted in FIG. 3. Prior to heater activation absolute humidity, capacitance, temperature, and relative humidity will have some non-zero value. Upon heater activation, the temperature measured may increase with time along temperature trend line 302. Capacitance may however decrease along a capacitance trend line 304 that may be an inversion of the temperature trend line 302. Relative humidity remains at a constant value along relative humidity trend line 306. Absolute humidity is linearly related capacitance, and may follow a trend line similar to capacitance trend line 304. FIG. 3 is normalized for a value of specific humidity for clarity and is not adjusted for uncertainty.

Using the aforementioned equations, relative humidity may be modeled in a disclosed embodiment, as a function of absolute humidity and temperature. FIG. 4A shows an example relationship between the modeled relative humidity and the actual relative humidity for an embodiment of the humidity sensor. The modeled relative humidity may be modeled after equation:

$$H_R = \frac{P_{H_2O}}{P_{Sat}}.$$

The measured relative humidity may be determined using equation:

$$H_R = \frac{P_{ambient}}{P_{Sat}} \frac{1}{1 + \frac{620.68 \, M}{H_A RT(P_{ambient} - P_{H_2O})}}$$

The water vapor pressure may be determined by a pressure sensor and the saturated vapor pressure may be calculated in response to the operating conditions, may be a predetermined value, or may be eliminated. An example modeled output and actual output that may be used in the control system for diagnostics are shown in FIG. 4A. The actual output variables ($H_A$ and T) and the modeled output variables ($P_{ambient}$ and $P_{Sat}$) may be sampled several times throughout the diagnostic test. The error between the actual relative humidity and the modeled relative humidity is shown in FIG. 4B. In this example the model value remained within 20% of the actual value.

In embodiments where a capacitive sensor within a humidity sensor reports RH in relative humidity, the control system may first compute a relative humidity based on a capacitive sensor output and a measured temperature. A pressure within the humidity sensor may be assumed and an absolute humidity calculated.

The sensor may report a relative humidity and a temperature. Using the absolute humidity calculated by the control system and the relative humidity reported by the sensor, an expected reported temperature may be computed. Other embodiments may compute an expected specific humidity or dew point. This may be compared to the reported temperature from the sensor for indications of degradation. Alternately, the absolute humidity computed by the control system and the temperature reported by the sensor may be used to determine an expected relative humidity. This expected relative humidity may be compared to the reported relative humidity for indications of degradation. The expected output may be referred to as the "modeled output". The reported output may be referred to as the "actual output".

FIG. 5A shows the same relationship as FIG. 4A for a degraded humidity sensor. Here the modeled output remains significantly higher than the actual output from the sensor. In this example, the percent error between the measurements reaches 70% as shown in FIG. 5B.

The error between the actual output and the modeled output over the sampling period is averaged for diagnostic runs on four different sensors in FIG. 6. The error found for a first sensor diagnostic 602 and a second sensor diagnostic 604 are, on average, below 20%. The error found for a third sensor diagnostic 606 and a fourth sensor diagnostic 608 are, on average, above 60%. The error distributions are plotted for first sensor diagnostic 602 and second sensor diagnostic 604 at first distribution line 610. The error distributions are plotted for third sensor diagnostic 606 and fourth sensor diagnostic 608 at second distribution line 612. If a sample distribution line has a distribution maximum above a threshold 600, such as line 612, degradation may be indicated.

In engine systems wherein a stable relative humidity can be maintained over a period of time, degradation may be indicated in some embodiments if the reported relative humidity changes during heater operation. Because relative humidity is a function of sensor output, unexpected unstable reported relative humidity within a temperature range may be indicative of a degradation of the temperature sensor and/or the sensor capacitor.

Alternate embodiments, such as that shown in FIG. 7 may, at a first condition, measure the capacitance of the sensor capacitor at 702 and measure the temperature within the humidity sensor at 704. At 706, a first absolute humidity $H_{A1}$ may be determined using a predetermined absolute humidity to capacitance relationship for the specific system. The local temperature may then be increased at 708 using a condensation heater that may be coupled to the temperature sensor and the capacitor within the humidity sensor. At a second condition, the local temperature $T_2$ may again be measured at 710. The capacitance of the sensor capacitor may be measured again at $T_2$ and the absolute humidity $H_{A2}$ may be found using the method of 706 at 710. The percent change of temperature may be determined by $\Delta T = T_1 - T_2/T_1$ at 716, similarly, the percent change of absolute humidity may be determined using $\Delta H = H_{A1} - H_{A2}/H_{A1}$ at 718. If the percent change of absolute humidity is not within a threshold error value of the percent change in temperature, degradation may be indicated. In other words, if a change of heat within the sampled engine air does not result in a change in absolute humidity of the sampled engine air within the measurement zone, degradation may be indicated.

It should be appreciated that the local temperature and the observed and expected effects on engine air, refer to the small sample of engine air within the humidity sensor and may not be applicable to the bulk engine airflow.

A temperature sensor diagnostic method is disclosed that may be performed additionally or alternatively to the other humidity sensor diagnostic methods and is depicted in FIG. 8. If a rational check is initiated, it may first be determined if the engine is off at 802. If the engine is not off the method may terminate. It may then be determined if rational check conditions are met, example rational check conditions may include ambient temperature or temperature within the engine system, humidity, thermal homogeneity throughout the engine system, or duration of engine key-off. Rational check conditions may, in some embodiments, include a 6 or more hour key-off engine soak.

If the rational check conditions are met at 804, it may be determined if the engine is in stable equilibrium at 806. Stable equilibrium may be determined by a number of ways, including monitoring engine conditions over a period of time or comparing engine conditions to known stable equilibrium conditions. If the engine is in stable equilibrium then a first temperature $T_1$ may be measured by the temperature sensor coupled to the humidity sensor at 808. This may be compared to temperature measurement $T_2$ by a second temperature sensor located within the engine system at 810. In thermal equilibrium the temperature in all parts of the engine system may be within a margin of error threshold that can be predetermined with much greater precision than during engine-on or unstable equilibrium. If the difference between $T_1$ and $T_2$ is not within the threshold at 812, degradation may be indicated at 816.

Stable equilibrium conditions may be specific to the locations of the first and second temperature sensor. Thus, the rational check of FIG. 8 may be performed when conditions would result in similar temperatures and temperature readings at the location of the first sensor and the location of the second sensor.

An additional temperature sensor check method is depicted in FIG. 9. Upon initiation at 900 it may be determined if the engine is on at 902. If the engine is operating then it may be determined if rational check conditions are met at 904. The conditions may include the passage of some amount of time since the last check was performed (so that the checks occur at regular intervals), presiding operating conditions, or an indication of following one or more of the methods disclosed herein. If conditions are met than the temperature within the humidity sensor may be determined using the coupled temperature sensor at 906. The engine may operate between a known temperature operating range wherein the minimum may be atmospheric temperature and the maximum may be maximum operating temperature. Thus, the temperature as determined by the sensor may be compared to known operating temperatures at 908. If the temperature sensor indicates that the temperature is outside the accepted range, degradation may be indicated at 910.

In another embodiment depicted in FIG. 10, the specific humidity may be measured or calculated from the absolute humidity and temperature. Relative humidity may be determined using a predefined relationship between capacitance and absolute humidity for a given humidity sensor. Temperature may be determined using a temperature sensor coupled to a humidity sensor or by another method not otherwise specified herein.

At 924 the relative humidity may be calculated for the given specific humidity, wherein the ambient pressure may be measured by a pressure sensor within the system, or a predetermined set value used for the system or operating conditions. Similarly, the saturated vapor pressure may be a set value predetermined for the system or may be based on one or more sensor measurements. A relative humidity range may be predetermined for certain operating systems. The range may be between the maximum possible relative humidity (100%) and the minimum observed relative humidity (~20%); it may also be an alternate predetermined range where a minimum relative humidity threshold and a maximum relative humidity threshold are determined. If the relative humidity is found to be between the minimum and maximum threshold at 926, the degradation check may terminate at 930. If the relative humidity is found to be outside of the range at 926, degradation may be indicated at 928.

Further embodiments, such as that depicted in FIG. 11, may include diagnosing humidity sensor degradation by measuring the temperature at a first condition using the temperature sensor coupled to the humidity sensor at 942. At 944, the local temperature within the humidity sensor may be increased using a condensation heater coupled to the humidity sensor. A second temperature may be measured at 946 after a predetermined amount of time using the temperature sensor coupled to the humidity sensor. An accepted maximum temperature change and minimum temperature change may be determined for the system and duration of heater activation. If the observed temperature change is within the maximum and minimum temperature change threshold, the method may terminate at 952. If the observed temperature change is outside of the maximum and minimum temperature change threshold, degradation may be indicated at 952.

In some embodiments one or more of the above diagnostic methods may be used in conjunction. An example method combining the disclosed methods is indicated in FIG. 12. After the initiation of a humidity sensor diagnostic routine at 960, one of the aforementioned humidity sensor diagnostic routines may be performed. An example embodiment of the humidity sensor diagnostic performed at 960 may include one or more of the routines depicted in FIG. 7, FIG. 10, or the model error routine described above. If degradation is indicated at 964, a flag may be set within the control system at 966.

At 968, a temperature sensor diagnostic method may be performed on the temperature sensor within the humidity sensor. The temperature sensor diagnostic method may include any of the aforementioned temperature sensor diagnostic methods such as those depicted in FIG. 9 or FIG. 11. If degradation within the temperature sensor is indicated it may be determined if the flag was set in the control system at 966. If a flag had been set at 966 then degradation may be indicated within the temperature sensor of the humidity sensor. If a flag had not been set at 966 then it may be determined that degradation has occurred within the condensation heater. This is because the humidity sensor diagnostic methods disclosed herein rely on the temperature sensors measurements, thus a degraded condensation heater may not affect the diagnosis of the humidity sensor based on relative, specific, or absolute humidity.

If temperature sensor degradation is not indicated at 972, then it may again be determined if a flag was set in the control system at 966. If a flag was set at 966, degradation within the humidity sensors capacitance sensor may be indicated at 978. If the flag was not set the process may terminate at 980. By this method degradation within the humidity sensor may be determined, further, the component contributing to the degradation may be determined so that the component may be replaced or repaired without replacing the entire sensor or performing additional timely or expensive diagnostics.

Note that the example control and estimation routines included herein can be used with various engine and/or vehicle system configurations. Further, this technology can be applied to any type of powertrain including, but not limited to, powertrains associated with pure electric, hybrid electric, plug-in hybrid electric, fuel cell electric, and diesel engine powered vehicles. The specific routines described herein may represent one or more of any number of processing strategies such as event-driven, interrupt-driven, multi-tasking, multi-threading, and the like. As such, various acts, operations, or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated acts or functions may be repeatedly performed depending on the particular strategy being used. Further, the described acts may graphically represent code to be programmed into the computer readable storage medium in the engine control system.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and nonobvious combinations and subcombinations of the various systems and configurations, and other features, functions, and/or properties disclosed herein.

The following claims particularly point out certain combinations and subcombinations regarded as novel and nonobvious. These claims may refer to "an" element or "a first" element or the equivalent thereof. Such claims should be understood to include incorporation of one or more such elements, neither requiring nor excluding two or more such elements. Other combinations and subcombinations of the disclosed features, functions, elements, and/or properties may be claimed through amendment of the present claims or through presentation of new claims in this or a related application.

Such claims, whether broader, narrower, equal, or different in scope to the original claims, also are regarded as included within the subject matter of the present disclosure.

The invention claimed is:

1. A method, comprising
    operating a sensor in an engine intake, a passage of the sensor including a temperature-sensing element, a heater, and a capacitance-sensing element; and
    individually distinguishing between each of heater, temperature-sensing element, and capacitance-sensing element degradation.

2. The method of claim 1 wherein an order of diagnostics among the heater, temperature-sensing element, and capacitance-sensing element degradation includes first determining whether overall degradation is present, and second determining temperature-sensing element degradation.

3. The method of claim 2 wherein the distinguishing is based on the first and second determination, and further includes indicating capacitance-sensing element degradation if overall degradation is present and temperature-sensing element degradation is not present, indicating temperature-sensing element degradation if overall degradation is not present and temperature-sensing element degradation is present, and indicating heater degradation if overall degradation is present and temperature-sensing element degradation is present.

4. The method of claim 3 wherein the overall sensor degradation is based on whether relative humidity is within a range.

5. The method of claim 3 wherein the overall sensor degradation is based on different absolute humidity determined at different temperatures.

6. The method of claim 3 wherein the overall sensor degradation is based on specific humidity.

7. A method for an engine system, comprising;
    indicating capacitance-based humidity sensor degradation, the sensor including a temperature sensor, in response to a measured humidity of the sensor; and
    indicating degradation within a component of the humidity sensor in response to temperature sensor degradation.

8. The method of claim 7, wherein the measured humidity is one or more of relative humidity, specific humidity, or absolute humidity.

9. The method of claim 8, further comprising indicating humidity sensor degradation if an error between a modeled humidity and the measured humidity exceeds a threshold.

10. The method of claim 8, further comprising determining a relative humidity based on a measured humidity and indicating humidity sensor degradation if the relative humidity falls above a predetermined relative humidity maximum or below a predetermined relative humidity minimum.

11. The method of claim 10, wherein the predetermined relative humidity maximum is between 90% and 100% and the predetermined relative humidity minimum is between 15% and 30%.

12. The method of claim 8, further comprising:
    at a first condition, measuring a temperature within the humidity sensor and measuring an absolute humidity;
    at a second condition, measuring the temperature within the humidity sensor and measuring the absolute humidity; and
    indicating humidity sensor degradation if a change in absolute humidity is not within a predetermined error range determined by a change in temperature.

13. The method of claim 8, further comprising:
- at a first condition, measuring a temperature, measuring an absolute humidity, and calculating a relative humidity or specific humidity;
- at a second condition, measuring the temperature, measuring the absolute humidity, and determining the relative humidity or specific humidity; and
- indicating humidity sensor degradation if a change in specific humidity is greater than a threshold.

14. The method of claim 13, wherein determining the threshold includes determining a vapor pressure, ambient pressure, partial pressure, or saturated pressure within the humidity sensor.

15. The method of claim 8, further comprising, during a first condition allowing the engine to equilibrate following a vehicle-off event, measuring a temperature within the humidity sensor using the temperature sensor, and measuring the temperature in one or more locations within the engine system using additional temperature sensors; and indicating temperature sensor degradation if the temperature sensor measurement does not fall between a range of values determined by the additional temperature sensors.

16. The method of claim 8, further comprising indicating temperature sensor degradation if the temperature sensor measures a temperature above 150 degrees Fahrenheit during a vehicle cruising condition.

17. The method of claim 8, further comprising indicating capacitance sensor degradation if humidity sensor degradation is indicated and temperature sensor degradation is not indicated.

18. The method of claim 8, further comprising indicating temperature sensor degradation if humidity sensor degradation is indicated and temperature sensor degradation is indicated.

19. A method, comprising
- operating a sensor in an engine intake of an engine coupled in a road vehicle, a passage of the sensor including a temperature-sensing element, a heater, and a capacitance-sensing element; and
- individually distinguishing between each of heater, temperature-sensing element, and capacitance-sensing element degradation; and
- indicating identified degradation by setting a diagnostic code.

20. The method of claim 19 wherein an order of diagnostics among the heater, temperature-sensing element, and capacitance-sensing element degradation includes first determining whether overall degradation is present, and second determining temperature-sensing element degradation, wherein the distinguishing is based on the first and second determination, and further includes indicating capacitance-sensing element degradation if overall degradation is present and temperature-sensing element degradation is not present, indicating temperature-sensing element degradation if overall degradation is not present and temperature-sensing element degradation is present, and indicating heater degradation if overall degradation is present and temperature-sensing element degradation is present.

* * * * *